(12) United States Patent
Pacetti (10) Patent No.: US 7,645,504 B1
(45) Date of Patent: *Jan. 12, 2010

(54) COATINGS FOR IMPLANTABLE MEDICAL DEVICES COMPRISING HYDROPHOBIC AND HYDROPHILIC POLYMERS

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 594 days.

This patent is subject to a terminal disclaimer.

(21) Appl. No.: 10/606,711

(22) Filed: Jun. 26, 2003

(51) Int. Cl.
*B32B 7/02* (2006.01)
*B32B 27/00* (2006.01)
*B32B 27/36* (2006.01)
*A61F 2/24* (2006.01)
*A61L 33/00* (2006.01)

(52) U.S. Cl. ............... 428/212; 428/34.1; 428/421; 428/480; 428/500; 428/522; 427/2.25; 427/2.1; 427/2.12; 427/2.24; 427/2.28; 427/2.3; 427/2.31; 427/331; 427/372.2; 427/377; 427/384; 427/337; 427/340; 623/1.1; 623/1.15; 623/1.42; 623/1.44; 623/1.46; 623/1.49; 623/23.57; 623/23.58; 623/23.59

(58) Field of Classification Search .............. 623/1.44, 623/1.45, 1.46, 1.49
See application file for complete search history.

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,977,901 A | 12/1990 | Ofstead | 128/772 |
| 5,112,457 A | 5/1992 | Marchant | 204/165 |
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,667,767 A | 9/1997 | Greff et al. | 424/9.411 |
| 5,670,558 A | 9/1997 | Onishi et al. | 523/112 |
| 5,700,286 A * | 12/1997 | Tartaglia et al. | 623/1.15 |
| 5,716,981 A | 2/1998 | Hunter et al. | 514/449 |
| 5,758,205 A | 5/1998 | Hara et al. | 396/79 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,231,600 B1 * | 5/2001 | Zhong | 623/1.42 |
| 6,908,624 B2 * | 6/2005 | Hossainy et al. | 424/424 |
| 6,926,919 B1 * | 8/2005 | Hossainy et al. | 427/2.25 |
| 7,008,979 B2 * | 3/2006 | Schottman et al. | 523/334 |
| 7,063,884 B2 * | 6/2006 | Hossainy et al. | 428/212 |
| 2002/0094440 A1 | 7/2002 | Llanos et al. | 428/421 |
| 2002/0111590 A1 | 8/2002 | Davila et al. | 604/265 |

FOREIGN PATENT DOCUMENTS

| | | |
|---|---|---|
| EP | 0 665 023 | 8/1995 |
| EP | 0 970 711 | 1/2000 |
| EP | 1 023 879 | 8/2000 |
| EP | 1 192 957 | 4/2002 |
| WO | WO 98/08463 | 3/1998 |
| WO | WO 00/12147 | 3/2000 |
| WO | WO 00/64506 | 11/2000 |
| WO | WO 01/01890 | 1/2001 |

* cited by examiner

*Primary Examiner*—Sheeba Ahmed
(74) *Attorney, Agent, or Firm*—Squire, Sanders & Dempsey L.L.P.

(57) ABSTRACT

Coatings for implantable medical devices and methods for fabricating thereof are disclosed. The coatings include a layer comprising a hydrophobic polymer and a layer comprising a hydrophilic or amphiphilic polymer.

27 Claims, 1 Drawing Sheet

FIG. 1

COATINGS FOR IMPLANTABLE MEDICAL DEVICES COMPRISING HYDROPHOBIC AND HYDROPHILIC POLYMERS

BACKGROUND OF THE INVENTION

1. Field of the Invention

This invention relates to the field of medical devices, particularly, devices used for delivery of drugs, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, the properties of stent coatings can be improved. For example, when the outermost layer of the coating comprises a blend of hydrophobic and hydrophilic polymers, the hydrophobic polymers tend to bloom to the coating-air interface. Yet, in many applications it is highly desirable to have hydrophilic polymers evolve at the coating-air interface to provide the stent coating with better blood compatibility, biological activity and non-fouling properties. Additionally, during the manufacturing process of the coating, as well as handling of the stent by a physician, contaminants can be introduced to the coating. The contaminants can produce adverse response at the implantation site. Accordingly, it is desirable to reduce contamination introduced by the coating to the region where the stent is implanted. The present application provides such coatings.

SUMMARY

According to one embodiment of the present invention, a method for fabricating a coating for an implantable medical device is provided, the method comprises forming a first layer of the coating on the device, the first layer including at least one hydrophobic polymer, and forming a water-soluble second layer of the coating on at least a portion of the first layer, the second layer including at least one hydrophilic or amphiphilic polymer. The hydrophobic polymers can include polymers having a Hildebrand solubility parameter lower than about 9.9 $(cal/cm^3)^{1/2}$. The hydrophilic polymers can include polymers having a Hildebrand solubility parameter higher than about 10.1 $(cal/cm^3)^{1/2}$. The amphiphilic polymers can include polymers having a Hildebrand solubility parameter between about 9.9 $(cal/cm^3)^{1/2}$ and about 10.1 $(cal/cm^3)^{1/2}$. The first layer of the coating can additionally include hydrophilic polymers which can be the same as, or different from, the hydrophilic polymer(s) included in the second layer.

According to another embodiment of the present invention, a coating for an implantable medical device is provided, the coating includes a first layer disposed on the device, the first layer including at least one hydrophobic polymer, and a second layer disposed on at least a portion of the first layer, the second layer including at least one hydrophilic or amphiphilic polymer. Examples of suitable hydrophobic polymers include poly(ethylene-co-vinyl alcohol), poly(vinyl acetate), poly(ethylene-co-vinyl acetate), poly(vinyl acetals), poly(m-ethyl methacrylate), poly(ethyl methacrylate), poly(n-propyl methacrylate), poly(iso-propyl methacrylate), poly(n-butyl methacrylate), poly(ethyl methacrylate-co-n-butyl methacrylate), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), poly(vinyl chloride), poly(vinyl fluoride), hexamethylene-1,6-diisocyanate-butanediol-co-polydimethylsiloxane, poly(vinylidene chloride), poly(vinylidene fluoride), poly(hexafluoropropene), poly(hexafluoropropene-co-vinylidene fluoride), poly(ethylene-co-hexafluoropropene), polytetrafluoroethylene, and blends thereof. Examples of suitable hydrophilic polymers include poly(propylene glycol), poly(ethylene oxide-co-propylene oxide), hyaluronic acid, poly(2-hydroxyethyl methacrylate), heparin, polyvinyl pyrrolidone), chondroitan sulfate, chitosan, glucosaminoglucans, dextran, dextrin, dextran sulfate, cellulose acetate, carboxymethyl cellulose, hydroxyethyl cellulose, cellulosics, poly(trimethylene glycol), poly(tetramethylene glycol), polypeptides, polyacrylamide, polyacrylimide, poly(ethylene amine), poly(allyl amine), and blends thereof. Examples of suitable amphiphilic polymers include poly(ethylene glycol) and poly(ethylene oxide).

According to yet another embodiment of the present invention, a method for fabricating a coating for an implantable medical device is provided, the method comprises forming a first layer of the coating on the device, the first layer including a hydrophobic polymer and a first hydrophilic or amphiphilic polymer, forming a water-soluble second layer of the coating on at least a portion of the first layer, the second layer including a second hydrophilic or amphiphilic polymer, and dissolving the second layer in an aqueous medium to produce a coating layer having higher concentration of the first hydrophilic or amphiphilic polymer on the outer surface thereof than the average concentration of the first hydrophilic or amphiphilic polymer throughout the coating layer.

DETAILED DESCRIPTION

Figure 1:
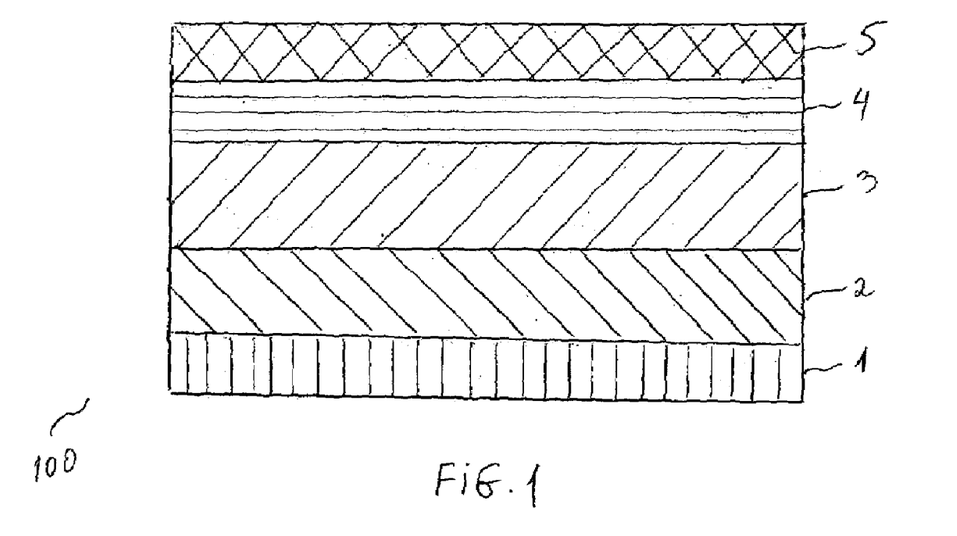
FIG. 1 is a schematic illustration of a cross-section of a stent coated according to one embodiment of the present invention.

As shown by FIG. 1, a coating 100 for an implantable medical device, such as a stent 1, according to one embodiment of the present invention, can include an optional primer layer 2, a drug-polymer layer 3 (also referred to as "reservoir" or "reservoir layer") or alternatively a polymer free drug layer 3, an optional topcoat layer 4, and a finishing coat layer 5. The drug-polymer layer 3 serves as a reservoir for the sustained release of the drug. The reservoir layer 3 or the polymer free drug layer can be applied directly onto the stent surface. The optional primer layer 2 can be applied on at least a portion of the stent surface to improve the adhesion of the drug-polymer layer 3 or the polymer free drug layer to the stent 1. The optional topcoat layer 4, which can be essentially free from any drugs, can be applied over at least a portion of the reservoir layer 3 and serves as a rate limiting membrane which helps to control the rate of release of the drug. The finishing coat layer 5 is the outermost layer of the stent coating 100. The finishing coat layer 5 is water-soluble and can be applied over at least a portion or the entire surface of the topcoat layer 4.

The optional primer layer 2, the reservoir layer 3, the topcoat layer 4, and the finishing coat layer 5 can be formed on the stent 1 by dissolving the polymer or a blend of polymers in a solvent, or a mixture of solvents, and applying the resulting polymer solution on the stent 1 by spraying or immersing the stent 1 in the solution. To incorporate a drug into the reservoir layer 3, the drug in a form of a solution can be combined with the polymer solution. Alternatively, to fabricate a polymer free drug layer, the drug can be dissolved in a suitable solvent or mixture of solvents, and the resulting drug solution can be applied on the stent 1 by spraying or immersing the stent in the drug solution.

Instead of introducing the drug in a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art will select the suitable solvent to form the solvent phase of the suspension, as well as the quantity of the drug to be dispersed in the solvent phase. The suspension can be mixed with a polymer solution and the mixture can be applied on the stent 1 as described above. Alternatively, the drug suspension can be applied on the stent without being mixed with the polymer solution.

The reservoir layer 3 and/or the topcoat layer 4 of the stent coating can include a hydrophobic polymer or a blend of several hydrophobic polymers. The hydrophobic polymer(s) can be water insoluble. The term "water insoluble" is defined as a polymer which can only form a stable aqueous solution containing at equilibrium less than about 2 mass % of the polymer. In the reservoir layer 3 and/or the topcoat layer 4, optionally, the hydrophobic polymer(s) can be blended with one or more hydrophilic polymers.

The finishing coat layer 5 can be free of hydrophobic polymers and any drugs and can include a hydrophilic polymer or a blend of several hydrophilic polymers. Should the hydrophilic polymer(s) be included in the reservoir layer 3 and/or the topcoat layer 4, the hydrophilic polymer(s) included in the finishing coat layer 5 can be the same as, or different from the hydrophilic polymer(s) included in the topcoat layer 4. The hydrophilic polymers can be water soluble. The term "water soluble" is defined as a polymer which can form a stable aqueous solution containing at equilibrium about 2 mass % of the polymer or more.

Generally, hydrophobicity of a polymer can be gauged using the Hildebrand solubility parameter δ. The term "Hildebrand solubility parameter" refers to a parameter indicating the cohesive energy density of a substance. The δ parameter is determined as follows:

$$\delta = (\Delta E/V)^{1/2}$$

where

δ is the solubility parameter, $(cal/cm^3)^{1/2}$;

ΔE is the energy of vaporization, cal/mole; and

V is the molar volume, $cm^3$/mole.

If a blend of a hydrophobic and hydrophilic polymer(s) is used, whichever polymer in the blend has lower δ value compared to the δ value of the other polymer in the blend is designated as a hydrophobic polymer, and the polymer with higher δ value is designated as a hydrophilic polymer. If more than two polymers are used in the blend, then each can be ranked in order of its δ value. For the practice of the present invention, the value of δ of a particular polymer is inconsequential for classifying a polymer as hydrophobic or hydrophilic. In one exemplary embodiment, the δ value defining the boundary between the hydrophobic and hydrophilic components of the polymer blend can be between about 9.9 and 10.1 $(cal/cm^3)^{1/2}$. According to this exemplary embodiment, the hydrophobic components of the polymer blend can have the δ value of below about 9.9 $(cal/cm^3)^{1/2}$, and the hydrophilic components can have the δ value of about 10.1 $(cal/cm^3)^{1/2}$ or higher.

The polymers occupying the boundary separating the hydrophobic and hydrophilic polymers (that is, having the δ value between about 9.9 and 10.1 $(cal/cm^3)^{1/2}$) can exhibit behavior characterizing both hydrophilic and hydrophobic polymers. Such polymers are defined as "amphiphilic." For the practice of the present invention, amphiphilic polymers can be used either as hydrophobic or as hydrophilic polymers. To illustrate, in one embodiment requiring a reservoir 3 and/or topcoat layer 4, both or either of which are to include a blend of hydrophobic and hydrophilic polymer(s), a blend can be used in which amphiphilic polymer(s) is mixed with either hydrophobic or hydrophilic polymer(s). Furthermore, amphiphilic polymer(s) can be used instead of, or in addition to, hydrophilic polymer(s) to manufacture a finishing coat layer 5. Examples of suitable amphiphilic polymers include poly(ethylene glycol)(PEG) and poly(ethylene oxide)(PEO). Both PEG and PEO have the δ value of about 9.9 $(cal/cm^3)^{1/2}$.

Poly(ethylene-co-vinyl alcohol) (EVAL) having a molar content of ethylene-derived units of more than about 44% is one example of a polymer that can be used to fabricate the primer layer 2, the reservoir layer 3, and/or the topcoat layer 4. EVAL is a product of hydrolysis of ethylene-vinyl acetate copolymers and may also include a terpolymer having up to about 5 molar % of units derived from styrene, propylene and other suitable unsaturated monomers. The Hildebrand parameter δ of this brand of EVAL is about 10.7 $(cal/cm^3)^{1/2}$. A brand of copolymer of ethylene, and vinyl alcohol distributed commercially under the trade name EVAL by Aldrich Chemical Co. of Milwaukee, Wis., can be used. In some embodiments, alternative polymers, which are at least as hydrophobic as EVAL (i.e. having the Hildebrand parameter δ of about 10.7 $(cal/cm^3)^{1/2}$ or lower, for example, lower than about 9.9 $(cal/cm^3)^{1/2}$, or blends thereof, can be included in the primer layer 2, the reservoir layer 3, and/or the topcoat layer 4.

Examples of such alternative hydrophobic polymers include poly(vinyl acetate), poly(ethylene-co-vinyl acetate), poly(vinyl acetals) such as poly(vinyl butyral) (e.g., BUTVAR), poly(meth)acrylates, for example, poly(methyl methacrylate), poly(ethyl methacrylate), poly(n-propyl methacrylate), poly(iso-propyl methacrylate), poly(n-butyl methacrylate), copolymers of butyl n-methacrylate with non-polar monomers (e.g., poly(ethyl methacrylate-co-n-butyl methacrylate)), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), styrene-butadiene-styrene triblock copolymers, styrene-ethylene/butylene-styrene triblock copolymers (e.g., KRATON available from Shell Oil, Co. of Houston, Tex.), styrene-isobutylene-styrene triblock copolymers, and parylene-C. In addition, the suitable hydrophobic polymers include organosilicon polymers (e.g., ELASTEON), and halogenated (e.g., fluorinated or chlorinated) polymers such as poly(vinyl chloride), poly(vinyl fluoride), poly(vinylidene chloride), poly(vinylidene fluoride) (e.g., KYNAR available from Atofina Chemicals, Inc. of Philadelphia, Pa.), poly(hexafluoropropene), poly(vinylidene fluoride-co-hexafluoropropene) (e.g., SOLEF available from Solvay S.A. of Brussels, Belgium), poly(ethylene-co-hexafluoropropene), and various grades of amorphous TEFLON, including polytetrafluoroethylene (available from E.I. Du Pont de Nemours & Co. of Wilmington, Del.).

BUTVAR is a trade name of poly(vinyl butyral) available from Solutia, Inc. of St. Louis, Mo. Typical brands of BUTVAR can include:

(1) terpolymer having about 80 mass % of vinyl butyral-derived units, about 19 mass % of vinyl alcohol-derived units, and the balance vinyl acetate-derived units;

(2) terpolymer having about 80 mass % of vinyl butyral-derived units and the balance vinyl alcohol-derived units; and (3) terpolymer having about 88 mass % of vinyl butyral-derived units, about 11 mass % of vinyl alcohol-derived units, and the balance vinyl acetate-derived units.

ELASTEON is the trade name of the block copolymer of methylene diphenyl diisocyanate, 1,4-butanediol, polyhexamethyleneglycol, and a carbinol terminated polydimethylsiloxane, manufactured by AorTech Biomaterials Co. of Chatswood, Australia.

As mentioned above, PEG and PEO are examples of amphiphilic polymers that can be utilized for making the topcoat layer 4 and the finishing coat layer 5. Brands of PEG and PEO that can be used can have molecular weight between about 15,000 and 40,000 Daltons, for example, about 17,500 Daltons to allow renal clearance of PEG and PEO.

In some embodiments, alternative polymers, which are at least as hydrophilic as PEG and PEO (i.e., having the Hildebrand parameter δ of about 9.9 $(cal/cm^3)^{1/2}$ or higher) can be used for making the topcoat layer 4 and the finishing coat layer 5. Examples of such alternative hydrophilic polymers include hyaluronic acid, poly(2-hydroxyethyl methacrylate), heparin, poly(vinyl pyrrolidone), chondroitan sulfate, chitosan, glucosaminoglycans, dextran, dextrin, dextran sulfate, cellulose acetate, carboxymethyl cellulose, hydroxyethyl cellulose, cellulosics, poly(propylene glycol), poly(ethylene oxide-co-propylene oxide) (e.g., PLURONIC available from BASF Corp. of Parsippany, N.J.), poly(trimethylene glycol), poly(tetramethylene glycol), polypeptides, polyacrylamide, polyacrylimide, poly(ethylene amine), and poly(allyl amine). To allow renal clearance of hydrophilic polymers other than PEG, the hydrophilic polymer that can be used can have molecular weight between about 10,000 and 40,000 Daltons, for example, about 30,000 Daltons.

To incorporate a blend of hydrophobic polymer(s) and hydrophilic polymer(s) in the reservoir 3 and/or topcoat layer 4, the hydrophobic polymer(s) can be blended with the hydrophilic polymer(s) and the blend can then be dissolved in a solvent or in a system comprising a mixture of solvents. Such solvent or the solvent system is selected that both the hydrophobic polymer(s) and the hydrophilic polymer(s) are solvable in the solvent or the solvent system. Alternatively, the hydrophobic polymer(s) and the hydrophilic polymer(s) can be dissolved separately to obtain a solution of the hydrophobic polymer(s) and a solution of the hydrophilic polymer(s), followed by combining the two solutions. As another alternative, the hydrophobic polymer(s) can be dissolved first to form the hydrophobic polymer solution, followed by adding the hydrophilic polymer(s) to the hydrophobic polymer solution. As yet another alternative, the hydrophilic polymer(s) can be dissolved first to form the hydrophilic polymer solution followed by adding the hydrophobic polymer(s) to the hydrophilic polymer solution.

The total amount of solids in the solution of the blend of the hydrophobic and hydrophilic polymer(s) can be between about 1 and about 5 mass %, for example, about 2 mass %. "Solids" means the amount of the dry residue deposited on a substrate after all volatile organic compounds of the solution (e.g., the solvent) have been removed. A ratio between the hydrophobic and hydrophilic polymer(s) in the solution of the blend of the hydrophobic and hydrophilic polymer(s) can be between about 99:1 and about 1:1, for example, between about 49:1 and about 19:1, such as about 25:1. For example, for a solution of the blend of the hydrophobic and hydrophilic polymer(s) containing about 2 mass % of the hydrophobic polymer(s), the concentration of the hydrophilic polymer(s) can be between about 0.04 and about 0.1 mass % of the total mass of the solution.

The solution of the blend of the hydrophobic and hydrophilic polymer(s) obtained by one of the methods discussed above can be then applied on the stent 1 by a commonly known technique known to those having ordinary skill in the art, for example, by spraying or dipping, followed by drying, for example, by baking, to form the reservoir and/or topcoat layer. Slow evaporating, strong solvents can be used, for example, N,N-dimethylacetamide (DMAC), N,N-dimethylformamide (DMF), or dimethylsulfoxide (DMSO).

Representative examples of other some suitable solvents include cyclohexanone, tetrahydrofuran (THF), xylene, toluene, acetone, i-propanol, methyl ethyl ketone, propylene glycol monomethyl ether, methyl butyl ketone, ethyl acetate, n-butyl acetate, chloroform, trichloroethane, trichloroethylene, and dioxane. Some solvent mixtures can be used as well. Representative examples of the mixtures include:

(1) DMAC and methanol (e.g., 50:50 by mass mixture);

(2) water, i-propanol, and DMAC (e.g., 10:3:87 by mass mixture);

(3) i-propanol, and DMAC (e.g., 80:20, 50:50, or 20:80 by mass mixtures);

(4) acetone and cyclohexanone (e.g., 80:20, 50:50, or 20:80 by mass mixtures);

(5) acetone and xylene (e.g. 50:50 by mass mixture); and (6) acetone, FLUX REMOVER AMS, and xylene (e.g., 10:50:40 by mass mixture).

FLUX REMOVER AMS is the trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer or blend of polymers being dissolved.

Should the hydrophilic polymer(s) be included in the reservoir 3 and/or topcoat layer 4, it is desirable for the hydrophilic polymer(s) to be miscible with the hydrophobic polymer(s) included in the topcoat layer 4. Hydrophilic, hydrophobic and/or amphiphilic polymer(s) comprising the polymeric blend are considered "miscible" if they satisfy at least one of the following two requirements:

(a) no visible phase separation occurs in the dried coating corn posed of the blend of the hydrophobic and hydrophilic polymer(s) prepared as described above; or (b) no thermal transitions (e.g., melting or glass transition) attributable to the individual components will be present in the dried coating comprising the polymer blend.

Thermal transitions can be detected by submitting the polymer blend to thermal analysis. Any standard method of thermal analysis, for example, differential scanning calorimetry (DSC), can be used. Those having ordinary skill in the art can determine which hydrophilic polymer(s) are miscible with the selected hydrophobic polymer(s).

In one embodiment of the invention, the stent coating 100 includes a primer layer 2, a reservoir layer 3, a topcoat layer 4, and a finishing coat layer 5, where the topcoat layer 4 is comprised of a blend of EVAL with PEG, and the finishing coat layer 5 is comprised of PEG. The presence of PEG in the finishing coat layer 5 is expected to induce migration of PEG present in the EVAL/PEG blend of the topcoat layer 4 towards the topcoat layer/finishing coat layer interface. As a result, the region of the topcoat layer 4 close to the interface can be enriched with PEG relative to the rest of the topcoat layer 4. In other words, a gradient of concentration of PEG in the topcoat layer 4 can occur, where the highest concentration of PEG can be observed in the region adjacent the topcoat layer/finishing coat layer interface, with gradual reduction in the PEG concentration in the underlying regions of the topcoat layer 4. The lowest concentration of PEG in the topcoat layer 4 can be observed in the area adjacent the topcoat layer/reservoir interface. A similar effect is expected when the stent coating 100 does not have the topcoat layer 4, but includes a reservoir 3 comprising EVAL/PEG blend and a finishing coat layer 5 comprising PEG. In this case, after the finishing coat layer 5 has been dissolved; the stent coating will include the reservoir layer 3, the outer surface of which and the region adjacent the outer surface will be enriched with PEG, and the gradient of the PEG concentration can exist throughout the reservoir 3.

When the stent 1 is implanted and comes in contact with aqueous body fluids, i.e., blood, the finishing coat layer 5 is expected to dissolve quickly, due to water solubility of a hydrophilic and/or amphihilic polymer(s) comprising the finishing coat layer 5. Generally, the process of dissolving the finishing coat layer 5 can take between about 1 and 30 minutes. In this particular embodiment (having PEG as the amphiphilic polymer), the process of dissolving can take between about 1 and 20 minutes. After the finishing coat layer 5 has been dissolved, the topcoat layer 4 becomes the outermost layer of the stent coating 100. As pointed out above, at this point, the surface and the upper region adjacent the surface of the topcoat layer 4 are enriched with PEG. However, PEG of the topcoat layer 4 is not expected to be dissolved similar to PEG of the finishing coat layer, because macromolecules of PEG present in the topcoat layer 4 are expected to become physically entangled and intertwined with macromolecules of EVAL.

To provide for better entanglement of PEG macromolecules, the hydrophobic polymer in the blend can have a glass transition temperature ($T_g$) equal to or greater than the normal physiological temperature of the patient's body (37° C.). If a lesser degree of entanglement leading to slow release of PEG contained in the topcoat layer 4 is desired, all or part of EVAL can be optionally replaced by another hydrophobic polymer having $T_g$ lower than ~37° C., for example, by poly(n-butyl methacrylate)(PBMA).

As a result of the entanglement, PEG is immobilized on the outer surface and the region adjacent the outer surface of the stent coating 100, and a stent coating having non-fouling outer surface can be thus obtained. The term "non-fouling surface" is defined as a surface not capable of adsorbing or attracting proteins, or adsorbing or attracting only a minimal amount of proteins or less proteins than a coating not having non-fouling properties.

In another embodiment, the stent coating 100 includes a primer layer 2, a reservoir layer 3, a topcoat layer 4, and a finishing coat layer 5. The topcoat layer 4 is comprised of EVAL and contains no PEG, and the finishing coat layer 5 is comprised of PEG. When such coating is fabricated by spraying, certain amount of PEG, which is sprayed over the EVAL layer, is expected to mix with EVAL. To facilitate the formation of the PEG/EVAL mixture, a slow evaporating solvent can be used, e.g., DMAC, DMSO or DMF. Thus, after the coating has been dried or baked, the coating includes a topcoat layer which can contain some quantity of PEG which is expected to be immobilized by being physically entangled and intertwined with macromolecules of EVAL. When the stent 1 is implanted and comes in contact with blood, the finishing coat layer 5 is expected to dissolve quickly, leaving a stent coating having non-fouling, PEG-containing outer surface.

To fabricate the stent coating 100, other polymers can be used, in addition to, or instead of, the hydrophobic polymers mentioned above. Examples of suitable polymers include poly(hydroxyvalerate), poly(L-lactic acid), polycaprolactone, poly(caprolactone-co-ethylene glycol), poly(caprolactone-co-glycolic acid), poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), poly(glycerol-sebacate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, polyvinyl ethers (such as polyvinyl methyl ether), polyacrylonitrile, polyvinyl ketones, polyvinyl aromatics (such as polystyrene), polyvinyl esters, copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, poly(ethylene terephthalate-co-ethylene oxide), poly(butylene terephthalate-co-ethylene oxide), dextran and its derivatives, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Generally speaking, the active agent or the drug can include any substance capable of exerting a therapeutic or prophylactic effect in the practice of the present invention. The drug may include small molecule drugs, peptides, proteins, oligonucleotides, and the like. Examples of drugs include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, anti fibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, and rapamycin (available from Wyeth Pharmaceuticals of Madison, N.J., under the name sirolimus)-, tacrolimus, and dexamethasone. Structural derivatives or functional analogs of rapamycin, such as 40-O-(2-hydroxy) ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin, can also be used.

The coatings and methods of the present invention have been described with reference to a stent, such as a balloon expandable or self-expandable stent. The use of the coating is not limited to stents, however, and the coating can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELFNE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the present invention can be further illustrated by the following: set forth examples.

Example 1

A first composition can be prepared by mixing the following components:

(a) between about 1.0 mass % and about 15 mass %, for example, about 2.0 mass % EVAL; and (b) the balance, DMAC solvent.

The first composition can be applied onto the surface of a bare 13 mm TETRA stent (available from Guidant Corporation) by spraying and dried to form a primer layer. A spray coater can be used, having a 0.014 fan nozzle maintained at about 60° C. with a feed pressure of about 0.2 atm (about 3 psi) and an atomization pressure of about 1.3 atm (about 20 psi). About 70 μg of the wet coating can be applied. The primer can be baked at about 140° C. for about 2 hours, yielding a dry primer layer.

A second composition can be prepared by mixing the following components:

(a) between about 1.0 mass % and about 15 mass %, for example, about 2.0 mass % EVAL;

(b) between about 0.05 mass % and about 2.0 mass %, for example, about 1.0 mass % EVEROLIMUS; and (c) the balance, DMAC solvent.

The second composition can be applied onto the dried primer layer to form a reservoir layer, using the same spraying technique and equipment used for applying the primer layer. About 400 μg of the wet coating can be applied, followed by drying at about 50° C. for about 2 hours.

A third composition can be prepared by mixing the following components:

(a) between about 1.0 mass % and about 15 mass %, for example, about 2.0 mass % EVAL;

(b) between about 0:5 mass % and about 5.0 mass %, for example, about 1.0 mass % poly(ethylene glycol) (PEG) having number-averaged molecular weight between about 15,000 and 40,000 Daltons, for example, about 17,500 Daltons; and (c) the balance, a solvent mixture comprising DMAC and ethanol (EtOH) in a mass ratio DMAC:EtOH of about 4:1.

The third composition can be applied onto the dried reservoir layer to form a topcoat layer, using the same spraying technique and equipment used for applying the primer and the reservoir layers. About 200 μg of the wet coating can be applied, followed by drying, e.g., by baking as described above.

A fourth composition can be prepared by mixing the following components:

(a) between about 0.5% and about 5 mass %, for example, about 2.0 mass % PEG having a number averaged molecular weight between about 15,000 and 40,000 Daltons, for example, about 17,500 Daltons; and (b) the balance, a solvent mixture comprising chloroform and trichloroethane in a mass ratio of about 1:1.

The fourth composition can be applied onto the dried topcoat layer to form a finishing coat layer, using the same spraying technique and equipment used for applying the primer and reservoir layers. About 100 µg of the wet coating can be applied, followed by drying at about 50° C. for about 2 hours.

Example 2

A first composition can be prepared by mixing the following components:

(a) between about 1:0 mass % and about 5 mass %, for example, about 2 mass % poly(n-butyl methacrylate) (PBMA); and (b) the balance, a solvent mixture comprising acetone and xylene in a mass ratio of about 1:1.

The first composition can be applied onto the surface of a bare 13 mm PENTA stent (available from Guidant Corporation) by spraying using a spray coater described in Example 1, and dried to form a primer layer. About 100 µg of wet coating can be applied. The primer can be baked at about 80° C. for about 1 hour, yielding a dry primer layer.

A second composition can be prepared by mixing the following components:

(a) between about 1.0 mass % and about 10 mass %, for example, about 2.0 mass % poly(vinylidene fluoride-co-hexafluoropropene) (SOLEF 21508);

(b) between about 0.1 mass % and about 1 mass %, for example, about 0.6 mass % EVEROLIMUS;

(c) between about 0.01 mass % and about 0.5 mass %, for example, about 0.1 mass % PEG having a number average molecular weight between about 15,000 and 40,000 Daltons, for example, about 17,500 Daltons; and (d) the balance, a solvent mixture comprising acetone and cyclohexanone in a mass ratio of about 7:3.

The second composition can be applied onto the dried primer layer to form a reservoir layer, using the same spray technique and equipment used for applying the primer and reservoir layers. About 800 µg of wet coating can be applied, followed by drying in an oven at about 50° C. for about 2 hours.

A third composition can be prepared by mixing the following components:

(a) between about 0.5% and about 5 mass %, for example, about 2.0 mass % PEG having a number averaged molecular weight between about 15,000 and 40,000 Daltons, for example, about 17,500 Daltons; and (b) the balance, a solvent mixture comprising chloroform and trichloroethane in a mass ratio of about 1:1.

The third composition can be applied onto the dried reservoir layer to form a topcoat layer, using the same spraying technique and equipment used for applying the primer and reservoir layers. About 100 µg of the wet coating can be applied, followed by drying at about 50° C. for about 2 hours.

Example 3

A dry primer layer can be formed on the surface of a bare 13 mm PENTA stent, as described in Example 2.

A first composition can be prepared by mixing the following components:

(a) between about 0.5 mass % and about 5 mass %, for example, about 1.0 mass % SOLEF 21508;

(b) between about between about 0.5 mass % and about 5 mass %, for example, about 1.0 mass % PBMA;

(c) between about 0.1 mass % and about 2.0 mass %, for example, about 1.0 mass % EVEROLIMUS; and (d) the balance, a solvent mixture comprising acetone and cyclohexanone in a mass ratio of about 7:3.

The first composition can be applied onto the dried primer layer to form a reservoir layer, using the same spray technique and equipment used for applying the primer layer. About 500 µg of wet coating can be applied, followed by drying in an oven at about 50° C. for about 2 hours.

A second composition can be prepared by mixing the following components:

(a) between about 0.5 mass % and about 5 mass %, for example, about 2.0 mass % SOLEF 21508;

(b) between about 0.05% and about 2 mass %, for example, about 0.1 mass % PEG having a number averaged molecular weight between about 15,000 and 40,000 Daltons, for example, about 17,500 Daltons; and (c) the balance, a solvent mixture comprising acetone and dimethylacetamide in a mass ratio of about 1:1.

The second composition can be applied onto the dried reservoir layer to form a topcoat layer, using the same spraying technique and equipment used for applying the primer and reservoir layers. About 100 µg of the wet coating can be applied, followed by drying at about 50° C. for about 2 hours.

A third composition can be prepared by mixing the following components:

(a) between about 0.5% and about 5 mass %, for example, about 2.0 mass % PEG having a number averaged molecular weight between about 15,000 and 40,000 Daltons, for example, about 17,500 Daltons; and (b) the balance, a solvent mixture comprising chloroform and trichloroethane in a mass ratio of about 1:1.

The third composition can be applied onto the dried topcoat layer to form a finishing coat layer, using the same spraying technique and equipment used for applying the primer, the reservoir, and the topcoat layers. About 100 µg of the wet coating can be applied, followed by drying at about 50° C. for about 2 hours.

Example 4

A layer of PARYLENE-C can be deposited onto the surface of a bare 13 mm VISION stent (available from Guidant Corporation) using a method of thermal deposition to form a primer layer. PARYLENE-C is a trade name of a poly(para-xylylene)-based coating available from Specialty Coating Systems, Inc. of Indianapolis, Ind. The thickness of the primer layer can be about 2 µm. A thermal deposition system can be used consisting of a sublimation chamber, tubular cracking furnace, deposition chamber, and vacuum system.

A first composition can be prepared by mixing the following components:

(a) between about 0.5 mass % and about 5 mass %, for example, about 2.0 mass % poly(ethylene-co-vinyl acetate) (PEVA);

(b) between about 0.1 mass % and about 2.0 mass %, for example, about 1.0 mass % sirolimus drug; and (c) the balance, a solvent mixture comprising acetone and cyclohexanone in a mass ratio of about 7:3.

The first composition can be applied onto the primer layer to form a reservoir layer, using the same spray technique and equipment used for applying the primer layer of Example 1. About 500 μg of wet coating can be applied, followed by drying in an oven at about 50° C. for about 2 hours.

A second composition can be prepared by mixing the following components:

(a) between about 0.5 mass % and about 5 mass %, for example, about 2.0 mass % of PBMA;

(b) between about 0.05% and about 2 mass %, for example, about 0.1 mass % PEG having a number averaged molecular weight between about 15,000 and 40,000 Daltons, for example, about 17,500 Daltons; and (c) the balance, a solvent mixture comprising chloroform and trichloroethane in a mass ratio of about 1.1.

The second composition can be applied onto the dried reservoir layer to form a topcoat layer, using the same spraying technique and equipment used for applying the primer and reservoir layers. About 100 μg of the wet coating can be applied, followed by drying at about 50° C. for about 2 hours.

A third composition can be prepared by mixing the following components:

(a) between about 0.5% and about 5 mass %, for example, about 2.0 mass % PEG having a number averaged molecular weight between about 15,000 and 40,000 Daltons, for example, about 17,500 Daltons; and (b) the balance, a solvent mixture comprising chloroform and trichloroethane in a mass ratio of about 1:1.

The third composition can be applied onto the dried topcoat layer to form a finishing coat layer, using the same spraying technique and equipment used for applying the primer and reservoir layers. About 100 μg of the wet coating can be applied, followed by drying at about 50° C. for about 2 hours.

Example 5

A PARYLENE-C primer layer can be formed on the surface of a bare 13 mm VISION stent as described in Example 4.

A first composition can be prepared by mixing the following components:

(a) between about 0.5 mass % and about 5 mass %, for example, about 2.0 mass % poly(D,L-lactide);

(b) between about 0.5 mass % and about 5.0 mass %, for example, about 2.0 mass % EVEROLIMUS; and (c) the balance, a solvent mixture comprising acetone and cyclohexanone in a mass ratio of 7:3. The first composition can be applied onto the primer layer to form the reservoir layer, using the same spray technique and equipment used for applying the primer layer of Example 1. About 400 μg of wet coating can be applied, followed by drying in an oven at about 50° C. for about 2 hours.

A second composition can be prepared by mixing the following components:

(a) between about 0.5 mass % and about 5 mass %, for example, about 2.0 mass % poly(D,L-lactide);

(b) between about 0.05% and about 2 mass %, for example, about 0.1 mass % PEG having a number averaged molecular weight between about 15,000 and 40,000 Daltons, for example, about 17,500 Daltons; and (c) the balance, a solvent mixture comprising chloroform and trichloroethane in a mass ratio of about 1:1.

The second composition can be applied onto the dried reservoir layer to form a topcoat layer, using the same spraying technique and equipment used for applying the primer and reservoir layers. About 100 μg of the wet coating can be applied, followed by drying at about 50° C. for about 2 hours.

A third composition can be prepared by mixing the following components:

(a) between about 0.5% and about 5 mass %, for example, about 2.0 mass % PEG having a number averaged molecular weight between about 15,000 and 40,000 Daltons, for example, about 17,500 Daltons; and (b) the balance, a solvent mixture comprising chloroform and trichloroethane in a mass ratio of about 1:1.

The third composition can be applied onto the dried topcoat layer to form a finishing coat layer, using the same spraying technique and equipment used for applying the primer and reservoir layers. About 100 μg of the wet coating can be applied, followed by drying at about 50° C. for about 2 hours.

Example 6

A first composition can be prepared by mixing the following components:

(a) between about 1.0 mass % and about 5 mass %, for example, about 2 mass % EVAL; and (b) the balance, a solvent mixture comprising tetrahydrofuran and dimethylacetamide in a mass ratio of about 2:3.

The first composition can be applied onto the surface of a bare 13 mm PENTA stent as described in Example 3. About 100 μg of wet coating can be applied. The primer can be baked at about 140° C. for about 1 hour, yielding a dry primer layer.

A second composition can be prepared by mixing the following components:

(a) between about 1.0 mass % and about 10 mass %, for example, about 2.0 mass % EVAL;

(b) between about 0.1 mass % and about 1 mass %, for example, about 0.67 mass % EVEROLIMUS;

(c) between about 0.01 mass % and about 0.5 mass %, for example, about 0.2 mass % poly(N-vinyl pyrrolidone) having a number average molecular weight of about 30,000 Daltons; and (d) the balance, a solvent mixture comprising tetrahydrofuran and dimethylacetamide in a mass ratio of 2:3.

The second composition can be applied onto the dried primer layer to form a reservoir layer, using the same spray technique and equipment used for applying the primer layer. About 500 μg of wet coating can be applied, followed by drying in an oven at about 50° C. for about 2 hours.

A third composition can be prepared by mixing the following components:

(a) between about 0.5% and about 5 mass %, for example, about 2.0 mass % poly(N-vinyl pyrrolidone) having a number averaged molecular weight of about 30,000 Daltons; and (b) the balance, a solvent mixture comprising chloroform and trichloroethane in a mass ratio of about 1:1.

The third composition can be applied onto the dried reservoir layer to form a finishing coat layer, using the same spraying technique and equipment used for applying the primer and reservoir layers. About 100 μg of the wet coating can be applied, followed by drying at about 50° C. for about 2 hours.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a coating for an implantable medical device, the method comprising:

(a) forming a first layer of the coating on the device, the first layer including at least one hydrophobic polymer and at least one hydrophilic polymer; and (b) forming a water-soluble second layer of the coating on at least a portion of the first layer, the second layer including at least one hydrophilic or amphiphilic polymer, wherein the hydrophobic polymer and the hydrophilic polymer in the first layer have a mass ratio between about 49:1 and about 19:1.

2. The method of claim 1, wherein the implantable medical device is a stent.

3. The method of claim 1, wherein the hydrophobic polymer has a Hildebrand solubility parameter lower than about 9.9 $(cal/cm^3)^{1/2}$.

4. The method of claim 1, wherein the hydrophobic polymer is selected from a group consisting of poly(ethylene-co-vinyl alcohol) and poly(n-butyl methacrylate).

5. The method of claim 1, wherein the hydrophobic polymer is selected from a group consisting of poly(vinyl acetate), poly(ethylene-co-vinyl acetate), poly(vinyl acetals), poly(methyl methacrylate), poly(ethyl methacrylate), poly(n-propyl methacrylate), poly(iso-propyl methacrylate), poly(ethyl methacrylate-co-n-butyl methacrylate), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), poly(vinyl chloride), poly(vinyl fluoride), hexamethylene-1,6-diisocyanate-butanediol-co-polydimethylsiloxane, poly(vinylidene chloride), poly(vinylidene fluoride), poly(hexafluoropropene), poly(hexafluoropropene-co-vinylidene fluoride), poly(ethylene-co-hexafluoropropene), polytetrafluoroethylene, and blends thereof.

6. The method of claim 1, wherein the hydrophilic polymer of the first or second layer has a Hildebrand solubility parameter of higher than about 10.1 $(cal/cm^3)^{1/2}$.

7. The method of claim 1, wherein the hydrophilic polymer of the first or second layer is selected from a group consisting of poly(propylene glycol), poly(ethylene oxide-co-propylene oxide), hyaluronic acid, poly(2-hydroxyethyl methacrylate), heparin, poly(vinyl pyrrolidone), chondroitan sulfate, chitosan, glucosaminoglucans, dextran, dextrin, dextran sulfate, cellulose acetate, carboxymethyl cellulose, hydroxyethyl cellulose, cellulosics, poly(trimethylene glycol), poly(tetramethylene glycol), polypeptides, polyacrylamide, polyacrylimide, poly(ethylene amine), poly(allyl amine), and blends thereof.

8. The method of claim 1, wherein the amphiphilic polymer has a Hildebrand solubility parameter of between about 9.9 and about 10.1 $(cal/cm^3)^{1/2}$.

9. The method of claim 1, wherein the amphiphilic polymer is poly(ethylene glycol) or poly(ethylene oxide).

10. The method of claim 1, wherein the first layer further includes at least one amphiphilic polymer.

11. A coating for an implantable medical device, comprising:

(a) a first layer disposed on the device, the first layer including at least one hydrophobic polymer and at least one hydrophilic polymer; and (b) a water-soluble second layer disposed on at least a portion of the first layer, the second layer including at least one hydrophilic or amphiphilic polymer, wherein the hydrophobic polymer and the hydrophilic polymer in the first layer have a mass ratio between about 49:1 and about 19:1.

12. The coating of claim 11, wherein the hydrophobic polymer has a Hildebrand solubility parameter lower than about 9.9 $(cal/cm^3)^{1/2}$.

13. The coating of claim 11, wherein the hydrophobic polymer is selected from a group consisting of poly(ethylene-co-vinyl alcohol) and poly(n-butyl methacrylate).

14. The coating of claim 11, wherein the hydrophobic polymer is selected from a group consisting of poly(vinyl acetate), poly(ethylene-co-vinyl acetate), poly(vinyl acetals), poly(methyl methacrylate), poly(ethyl methacrylate), poly(n-propyl methacrylate), poly(iso-propyl methacrylate), poly(ethyl methacrylate-co-n-butyl methacrylate), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), poly(vinyl chloride), poly(vinyl fluoride), hexamethylene-1,6-diisocyanate-butanediol-co-polydimethylsiloxane, poly(vinylidene chloride), poly(vinylidene fluoride), poly(hexafluoropropene), poly(hexafluoropropene-co-vinylidene fluoride), poly(ethylene-co-hexafluoropropene), polytetrafluoroethylene, and blends thereof.

15. The coating of claim 11, wherein the hydrophilic polymer of the first or second layer has a Hildebrand solubility parameter of higher than about 10.1 $(cal/cm^3)^{1/2}$.

16. The coating of claim 11, wherein the hydrophilic polymer of the first or second layer is selected from a group consisting of poly(propylene glycol), poly(ethylene oxide-co-propylene oxide), hyaluronic acid, poly(2-hydroxyethyl methacrylate), heparin, poly(vinyl pyrrolidone), chondroitan sulfate, chitosan, glucosaminoglucans, dextran, dextrin, dextran sulfate, cellulose acetate, carboxymethyl cellulose, hydroxyethyl cellulose, cellulosics, poly(trimethylene glycol), poly(tetramethylene glycol), polypeptides, polyacrylamide, polyacrylimide, poly(ethylene amine), poly(allyl amine), and blends thereof.

17. The method of claim 11, wherein the amphiphilic polymer has a Hildebrand solubility parameter of between about 9.9 and about 10.1 $(cal/cm^3)^{1/2}$.

18. The coating of claim 11, wherein the amphiphilic polymer is poly(ethylene glycol) or poly(ethylene oxide).

19. The coating of claim 11, wherein the first layer further includes at least one amphiphilic polymer.

20. A method of surface modification of a coating on an implantable medical device, the method comprising:

(a) forming a first layer of the coating on the device, the first layer including a hydrophobic polymer and a first hydrophilic or amphiphilic polymer; and (b) forming a water-soluble second layer of the coating on at least a portion of the first layer, the second layer including a second hydrophilic or amphiphilic polymer; and (c) dissolving the second layer in an aqueous medium to produce a coating layer having higher concentration of the first hydrophilic or amphiphilic polymer on the outer surface thereof than the average concentration of the first hydrophilic or amphiphilic polymer throughout the coating layer.

21. The method of claim 20, wherein the hydrophobic polymer has a Hildebrand solubility parameter lower than about 9.9 $(cal/cm^3)^{1/2}$.

22. The method of claim 20, wherein the hydrophobic polymer is selected from a group consisting of poly(ethylene-co-vinyl alcohol) and poly(n-butyl methacrylate).

23. The method of claim 20, wherein the hydrophobic polymer is selected from a group consisting of poly(vinyl acetate), poly(ethylene-co-vinyl acetate), poly(vinyl acetals), poly(methyl methacrylate), poly(ethyl methacrylate), poly (n-propyl methacrylate), poly(iso-propyl methacrylate), poly(ethyl methacrylate-co-n-butyl methacrylate), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), poly(vinyl chloride), poly(vinyl fluoride), hexamethylene-1,6-diisocyanate-butanediol-co-polydimethylsiloxane, poly(vinylidene chloride), poly(vinylidene fluoride), poly(hexafluoropropene), poly(hexafluoropropene-co-vinylidene fluoride), poly(ethylene-co-hexafluoropropene), polytetrafluoroethylene, and blends thereof.

24. The method of claim 20, wherein each of the first and the second hydrophilic polymer has a Hildebrand solubility parameter of higher than about 10.1 $(cal/cm^3)^{1/2}$.

25. The method of claim 20, wherein each of the first and the second hydrophilic polymer is selected from a group consisting of poly(propylene glycol), poly(ethylene oxide-co-propylene oxide), hyaluronic acid, poly(2-hydroxyethyl methacrylate), heparin, poly(vinyl pyrrolidone), chondroitan sulfate, chitosan, glucosaminoglucans, dextran, dextrin, dextran sulfate, cellulose acetate, carboxylethyl cellulose, hydroxyethyl cellulose, cellulosics, poly(trimethylene glycol), poly(tetramethylene glycol), polypeptides, polyacrylamide, polyacrylimide, poly(ethylene amine), poly(allyl amine), and blends thereof.

26. The method of claim 20, wherein the each of the first and the second amphiphilic polymer has a Hildebrand solubility parameter of between about 9.9 and about 10.1 $(cal/cm^3)^{1/2}$.

27. The method of claim 26, wherein each of the first and the second amphiphilic polymer is poly(ethylene glycol) or poly(ethylene oxide).

* * * * *

UNITED STATES PATENT AND TRADEMARK OFFICE
CERTIFICATE OF CORRECTION

PATENT NO. : 7,645,504 B1  Page 1 of 1
APPLICATION NO. : 10/606711
DATED : January 12, 2010
INVENTOR(S) : Stephen D. Pacetti It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 817 days.

Signed and Sealed this

Twenty-eighth Day of December, 2010

David J. Kappos
*Director of the United States Patent and Trademark Office*